United States Patent
Chew et al.

(10) Patent No.: US 8,273,024 B2
(45) Date of Patent: Sep. 25, 2012

(54) ULTRASOUND TRANSMISSION GEL

(76) Inventors: Rita Kathleen Chew, S.E. Everett, WA (US); Richard Lawrence Mahan, Greenback, WA (US)

( * ) Notice: Subject to any disclaimer, the term of this patent is extended or adjusted under 35 U.S.C. 154(b) by 1217 days.

(21) Appl. No.: 11/079,027

(22) Filed: Mar. 14, 2005

(65) Prior Publication Data
US 2005/0215908 A1 Sep. 29, 2005

Related U.S. Application Data

(60) Provisional application No. 60/553,500, filed on Mar. 16, 2004.

(51) Int. Cl.
*A61B 8/00* (2006.01)
(52) U.S. Cl. ............................ 600/437; 601/2
(58) Field of Classification Search .......... 600/437–448, 600/567, 466, 410, 411; 606/41, 170, 167; 310/26; 525/178, 207
See application file for complete search history.

(56) References Cited

U.S. PATENT DOCUMENTS

| | | | |
|---|---|---|---|
| 4,088,751 A * | 5/1978 | Kenkare et al. | 424/47 |
| 5,522,814 A * | 6/1996 | Bernaz | 606/36 |
| 5,691,285 A | 11/1997 | Coffey et al. | 508/491 |
| 5,849,009 A | 12/1998 | Bernaz | 606/36 |
| 5,957,846 A * | 9/1999 | Chiang et al. | 600/447 |
| 6,136,329 A | 10/2000 | Boratyn | |
| 6,497,702 B1 | 12/2002 | Bernaz | |
| 6,554,771 B1 * | 4/2003 | Buil et al. | 600/459 |
| 6,607,716 B1 | 8/2003 | Smith et al. | |
| 6,623,517 B1 | 9/2003 | DeLuisa et al. | |
| 2001/0033825 A1 * | 10/2001 | Douglas | 424/9.5 |
| 2002/0082279 A1 | 6/2002 | Schultz | |
| 2002/0146474 A1 | 10/2002 | Tomatis | |
| 2003/0039709 A1 | 2/2003 | Thrash | |
| 2003/0059480 A1 | 3/2003 | Boratyn | |
| 2003/0083212 A1 | 5/2003 | Willard et al. | |
| 2003/0167004 A1 * | 9/2003 | Dines et al. | 600/437 |
| 2003/0190301 A1 | 10/2003 | Fry | |
| 2003/0211161 A1 | 11/2003 | Ahmad et al. | |

FOREIGN PATENT DOCUMENTS

| | | | |
|---|---|---|---|
| GB | 2236760 | | 4/1991 |
| JP | 2001/335429 | | 12/2001 |
| WO | WO 2005/004830 | * | 1/2005 |
| WO | WO 2005004830 A1 | * | 1/2005 |

* cited by examiner

*Primary Examiner* — Long V. Le
*Assistant Examiner* — Bradley Impink
(74) *Attorney, Agent, or Firm* — Kunzler Law Group, PC

(57) ABSTRACT

An improved ultrasound transmission gel adapted to induce a therapeutic effect and/or palliative effect in a patient. An ultrasound transmission gel may include a water-based gel having a conductivity adapted to facilitate ultrasound signal transfer, and an essential oil. An essential oil may be selected according to its ability to calm and/or relieve certain medical conditions. In some embodiments, an ultrasound transmission gel may be customized to suit a particular patient's medical needs.

6 Claims, 6 Drawing Sheets

| Essential Oils | Latin Names | Properties |
|---|---|---|
| Balsam (Wild Fir) | Abies siberica | Skin care |
| Chamomile | Matricaria, Ormensis, Chameamelum | Relaxation, sleep, balance, peace |
| Lavender | Lavandula | Calming, balancing, restful sleep |
| Rosewood | Aniba rosaeodora | Serenity, focus, spirituality |
| Sage | Salvis officinalis | Rejuvenation, alertness |
| Sandalwood | Santalum album | Tranquility, spirituality |
| Tangerine | Citrus reticulata | Inspiration, empathy, peace |
| Vanilla | Vanilla planifolia | Security, romance, sensuality |
| Ylang Ylang | Cananga odorata | Exhuberance, acceptance, sensuality |

FIG. 4

ULTRASOUND TRANSMISSION GEL

CROSS-REFERENCES TO RELATED APPLICATIONS

This application claims the benefit of U.S. Provisional Patent Application No. 60/553,500 entitled "Ultrasound Scanning Gel" and filed on Mar. 16, 2004 for Rita K. Chew and Richard L. Mahan.

BACKGROUND OF THE INVENTION

1. Field of the Invention

The present invention relates to an ultrasound transmission gel and, more particularly, to an improved ultrasound transmission gel having therapeutic and palliative properties.

2. Background

Ultrasound technology has a well established role in medical imaging, where high frequency sound waves are used to produce two-dimensional images to diagnose and/or monitor various medical conditions. As ultrasound imaging is non-invasive, virtually risk-free, and capable of producing almost instantaneous results, it is particularly useful in fields such as obstetrics and gynecology, cardiology, urology and oncology where the use of x-rays or other radiographic techniques may be prohibited, or where time is of the essence.

To obtain an image by ultrasound, high frequency sound waves, typically in a range from one to 12 megahertz, are transmitted through the skin by a probe. Sound waves are reflected back to the probe when they hit a boundary between materials having different acoustic impedances, such as between fluid and soft tissue, or between soft tissue and bone. The reflected sound waves are then transmitted to a central processing unit that calculates the distance from the probe to the boundary. The central processing unit displays the distances and intensities of the reflected sound waves on a screen as a two-dimensional image.

Ultrasound transmission gels are topically applied to an area of skin that covers a target tissue area to eliminate air between the probe and the skin as sound waves are transmitted to the tissue area. In this manner, an ultrasound transmission gel, or "scanning gel," not only acts as a lubricant between the probe and the skin, but also acts as a couplant to provide an acoustic pathway between the probe and the skin.

While known transmission gels effectively moderate ultrasound transmission between a probe and the skin, such gels generally fail to provide an independent palliative effect or therapeutic effect. In fact, although ultrasound imaging procedures are highly innocuous, it is not unusual for a patient to experience some degree of apprehension or discomfort during the procedure. Some patients may even suffer from pain, depending on the ailment being examined or treated. Known transmission gels may increase a patient's anxiety and discomfort due to the perception of cold upon application of the gel.

Accordingly, what is needed is an improved ultrasound transmission gel having properties capable of producing an independent palliative effect or therapeutic effect. Further what is needed is an improved ultrasound transmission gel capable of minimizing a perception of cold upon application. Finally what is needed is an improved ultrasound transmission gel having properties customizable to a patient's specific medical condition. Such compositions and methods are disclosed and claimed herein.

SUMMARY OF THE INVENTION

The present invention has been developed in response to the present state of the art, and in particular, in response to the problems and needs in the art that have not yet been fully solved by currently available ultrasound transmission gels. Accordingly, the present invention has been developed to provide an improved ultrasound transmission gel that overcomes many or all of the above-discussed shortcomings in the art.

An ultrasound transmission gel in accordance with certain embodiments of the present invention is presented to alleviate a patient's anxiety and/or discomfort during an ultrasound imaging procedure, or any procedure which requires a transmission gel including therapeutic physical therapy ultrasound gel. In one embodiment, an ultrasound transmission gel features a water-soluble gel appropriate for use in connection with ultrasound imaging techniques that includes at least one essential oil to induce a palliative effect or therapeutic effect in a patient. A water-soluble gel may be highly conductive to promote ultrasound signal transfer between a patient and ultrasound imaging equipment. In addition, a water-soluble gel may be substantially colorless, hypoallergenic and non-staining to permit its use in connection with various patients having various ailments and sensitivities.

An essential oil for use in connection with an ultrasound transmission gel in accordance with the present invention may include any essential oil capable of inducing a palliative effect or therapeutic effect in a patient. In some embodiments, an ultrasound transmission gel may be customized to include an essential oil specifically selected to alleviate a certain condition. An essential oil, for example, may be selected for its ability to reduce pain, encourage healing, boost vitality, or reduce stretch marks, nausea, or other medical condition. In other embodiments, an essential oil may be selected for its ability to relax, relieve stress or anxiety, or comfort mother and baby. An essential oil may include balsam, chamomile, lavender, rosewood, sage, sandalwood, tangerine, vanilla, ylang ylang, palma rosa, elemi, geranium, patchouli, rose, clary sage, bergamot or any other essential oil known to those in the art, and may make up one to five percent of the ultrasound transmission gel by weight.

In certain embodiments, an ultrasound transmission gel may include an exothermic agent capable of reducing a patient's perception of cold upon application of the ultrasound transmission gel. An exothermic agent may comprise, for example, methyl salicylate, phosphate derivatives, vanillyl derivatives, ethanol, niacin, eucalyptus oil, cinnamon cassia (cinnamon), zingiber officinalis (ginger), mint, sandalwood, orange, clove, amara (almond), persica gratissima (avocado oil), cannabis sativa (hemp) seed oil, aloe vera, or any other exothermic agent known to those in the art. Alternatively, an exothermic agent may comprise a heat-generating medium consisting of carbon, iron, water and/or salt which is activated upon contact with oxygen in the air. An exothermic composition may be substantially heat-retentive to promote a patient's continued comfort during an ultrasound imaging or transmission procedure.

A system of the present invention is also presented to reduce anxiety and/or discomfort experienced by a patient during an ultrasound imaging or transmission procedure. The system may be embodied by a probe configured to administer ultrasound signals to a target tissue area and receive information corresponding thereto, a processing device coupled to the probe to process the information and produce an image of the target tissue area, and an ultrasound transmission gel creating an interface between the probe and a patient to facilitate accurate ultrasound imaging. As discussed above, an ultrasound transmission gel may include a water-soluble gel having a conductivity adapted to facilitate ultrasound signal transfer and at least one essential oil to induce at least one of a palliative effect and a therapeutic effect in the patient.

A method of the present invention is also presented for reducing a patient's anxiety and/or discomfort during an ultrasound imaging procedure. In one embodiment, the method includes providing a water-soluble gel having a conductivity adapted to facilitate ultrasound signal transfer, selecting at least one essential oil adapted to induce a palliative effect or therapeutic effect, integrating with the water-soluble gel the essential oil to produce an ultrasound transmission gel, topically applying the ultrasound transmission gel to the patient at a location substantially corresponding to a target tissue area, and imaging the target tissue area with ultrasound scanning equipment. In certain embodiments, an essential oil may be specifically selected according to its known properties to relieve a condition from which the patient suffers, such as stress, pain, nausea, depression and discomforts of pregnancy. In this manner, the present invention enables an ultrasound scanning or transmission gel to be customized to a particular patient.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

In order that the manner in which the above recited and other features and advantages of the present invention are obtained, a more particular description of the invention will be rendered by reference to specific embodiments thereof, which are illustrated in the appended drawings. Understanding that the drawings depict only typical embodiments of the present invention and are not, therefore, to be considered as limiting the scope of the invention, the present invention will be described and explained with additional specificity and detail through the use of the accompanying drawings in which:

FIG. 4 is a table listing some characteristics of selected essential oils that may be implemented in accordance with certain embodiments of the present invention;

DETAILED DESCRIPTION OF THE INVENTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

As used in this specification, the term "patient" refers to any human or animal species subject to an ultrasound imaging procedure or an ultrasound transmission procedure. The term "target tissue area" or "target tissue" refers to an area of tissue subjacent an epidermal layer of a patient that is the subject of an ultrasound imaging procedure or an ultrasound transmission procedure. The terms "transmission gel," "gel," or "scanning gel" are used herein interchangeably and refer to any substantially viscous composition capable of conducting ultrasound signals to and from a target tissue. The term "essential oil" refers to an oil extracted from plants, flowers, grass, stems, seeds, leaves, roots, bark, fruits, tree moss or trees.

Figure 1:
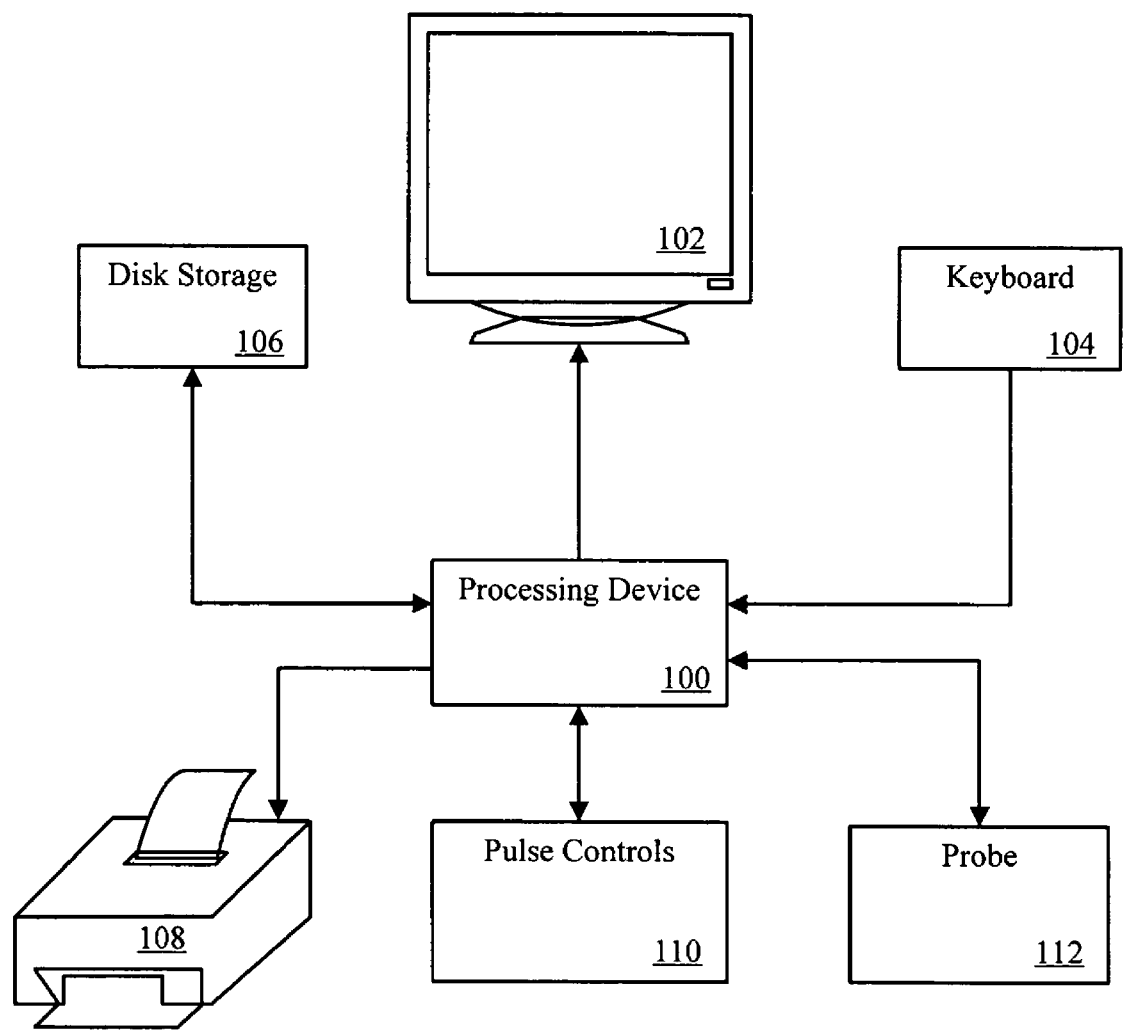
FIG. 1 is a plan diagram of ultrasound imaging equipment in accordance with certain embodiments of the present invention.

Referring to FIG. 1, an ultrasound transmission gel in accordance with the present invention may be topically applied as an interface between ultrasound scanning equipment and a target tissue area. Ultrasound scanning equipment may generally include a processing device 100 and various peripheral components such as a monitor 102, keyboard 104, disk storage device 106, printer 108, pulse controls 110, and a probe 112.

A processing device 100 generally comprises a computer that contains the microprocessor, memory, amplifiers and power supplies for the processing device 100 and probe 112. In operation, the processing device 100 sends electrical currents to a probe 112 which may be emitted as ultrasound signals, or sound waves, towards a target tissue area. When the sound waves hit a boundary between tissues, such as between fluid and soft tissue or between soft tissue and bone, some of the sound waves may be reflected back to the probe 112. The probe 112 may relay such reflected sound waves back to the processing device 100 as electrical currents. Information relating to sound waves emitted and sound waves received is processed by the processing device 100 to create an ultrasound image of the target tissue area on the monitor 102. Specifically, the processing device 100 may calculate the distance from the probe 112 to the boundary from which a sound wave is reflected using the speed of sound in tissue and the time it takes for the sound wave to be reflected. The processing device 100 may display the distances and intensities of the reflected sound waves on a monitor 102 in the form of a two-dimensional image.

The processing device 100, with the aid of a disk storage device 106, may also store the image and/or information on a hard disk, floppy disk, compact disk, digital video disk, or any other storage device known to those in the art. A printer 108 connected to the processing device 100 may be used to capture a hard copy of the image from the monitor 102. A keyboard 104 connected to the processing device 100 may enable an operator to add notes and take measurements from the image and/or other information obtained by the probe 112 and processing device 100.

As mentioned previously, a probe 112 may be connected to a processing device 100 to send and receive sound waves to and from a target tissue area. Specifically, a probe 112 may contain one or more piezoelectric crystals that respond to an electric current generated by the processing device 100 by vibrating. Such vibrations produce sound waves that may be directed toward a target tissue area. Similarly, sound waves reflected by a boundary in the target tissue area cause the piezoelectric crystals to generate an electrical current. In this manner, the probe 112 may be used to both send and receive sound waves to and from a target tissue area, and to send and receive data in the form of electrical currents to and from the processing device 100. In some embodiments, a probe 112 may include a sound absorbing substance (not shown) such as silicon, epoxy or plastic to eliminate back reflections from the probe itself, and may further include an acoustic lens (not shown) to focus emitted sound waves.

In certain embodiments, pulse controls 110 in communication with the processing device 100 enable an operator to establish and adjust the frequency and duration of sound waves emitted by the probe 112 according to specific target tissue area characteristics.

Figure 2:
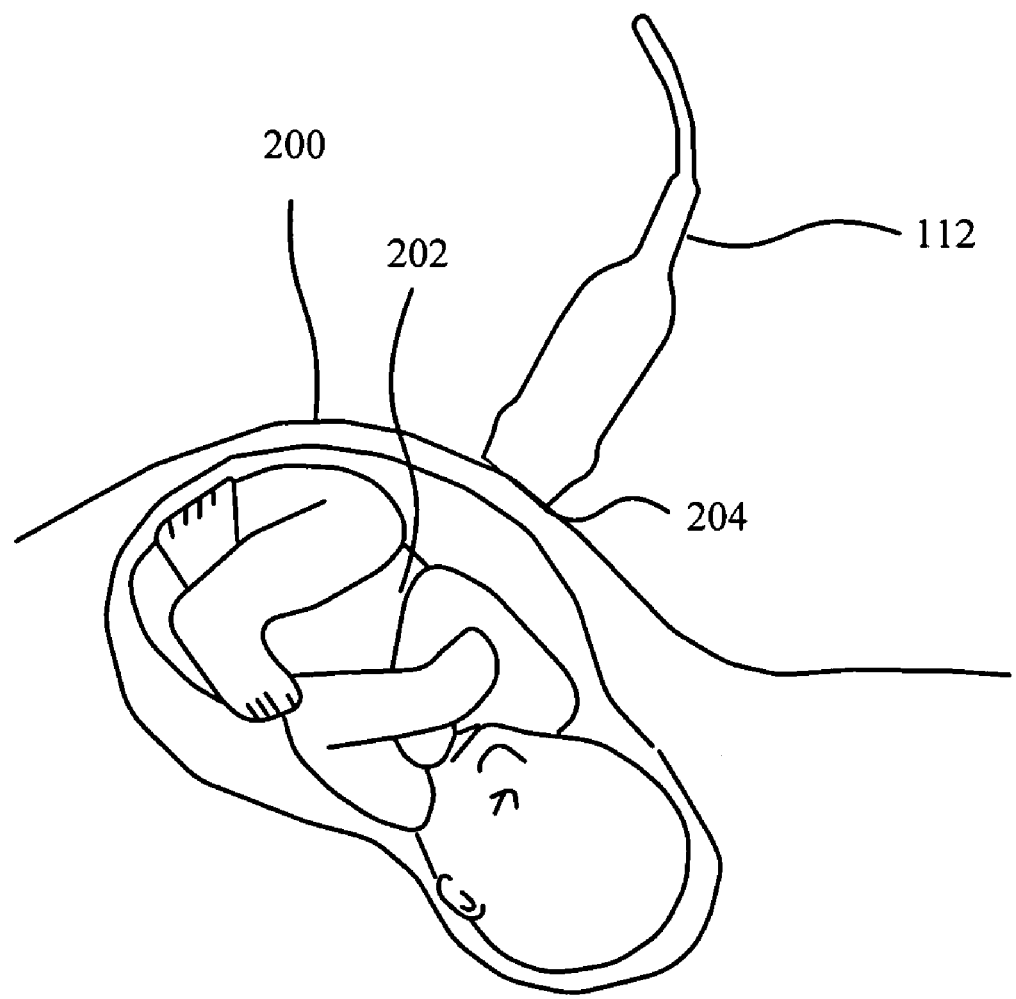
FIG. 2 is a cross-sectional view of a patient undergoing an ultrasound imaging procedure in accordance with the present invention.

Referring now to FIG. 2, an ultrasound transmission gel 204 in accordance with the present invention may be implemented to interface between a probe 112 and a patient's skin 200 to facilitate sound wave transfer between the probe 112 and a target tissue 202. Specifically, an ultrasound transmission gel 204 may be applied to an area of a patient's skin 200 substantially corresponding to a target tissue area 202. A probe 112 may then be applied to substantially the same area 200 to transmit and receive sound waves to and from the target tissue 202. As an ultrasound transmission gel 204 in accordance with the present invention may intimately contact both the probe 112 and a patient's skin 200, the ultrasound transmission gel 204 preferably comprises components inherently safe for both. In certain embodiments, for example, an ultrasound transmission gel 204 may be colorless, hypoallergenic and/or non-staining.

Further, the present invention contemplates utilizing the inherently intimate relationship between an ultrasound transmission gel 204 and a patient's skin 202 to confer independent and, in some embodiments, customizable benefits to a patient. An ultrasound transmission gel 204 may, for example, include one or more essential oils to provide an independent beneficial effect to a patient during an ultrasound procedure. As discussed in more detail with reference to FIG. 4 below, certain essential oils are known to provide specific beneficial effects. Where an ultrasound transmission gel 204 includes one or more essential oils, a patient may immediately benefit from its effects, thereby facilitating accurate ultrasound imaging results.

Figure 3:
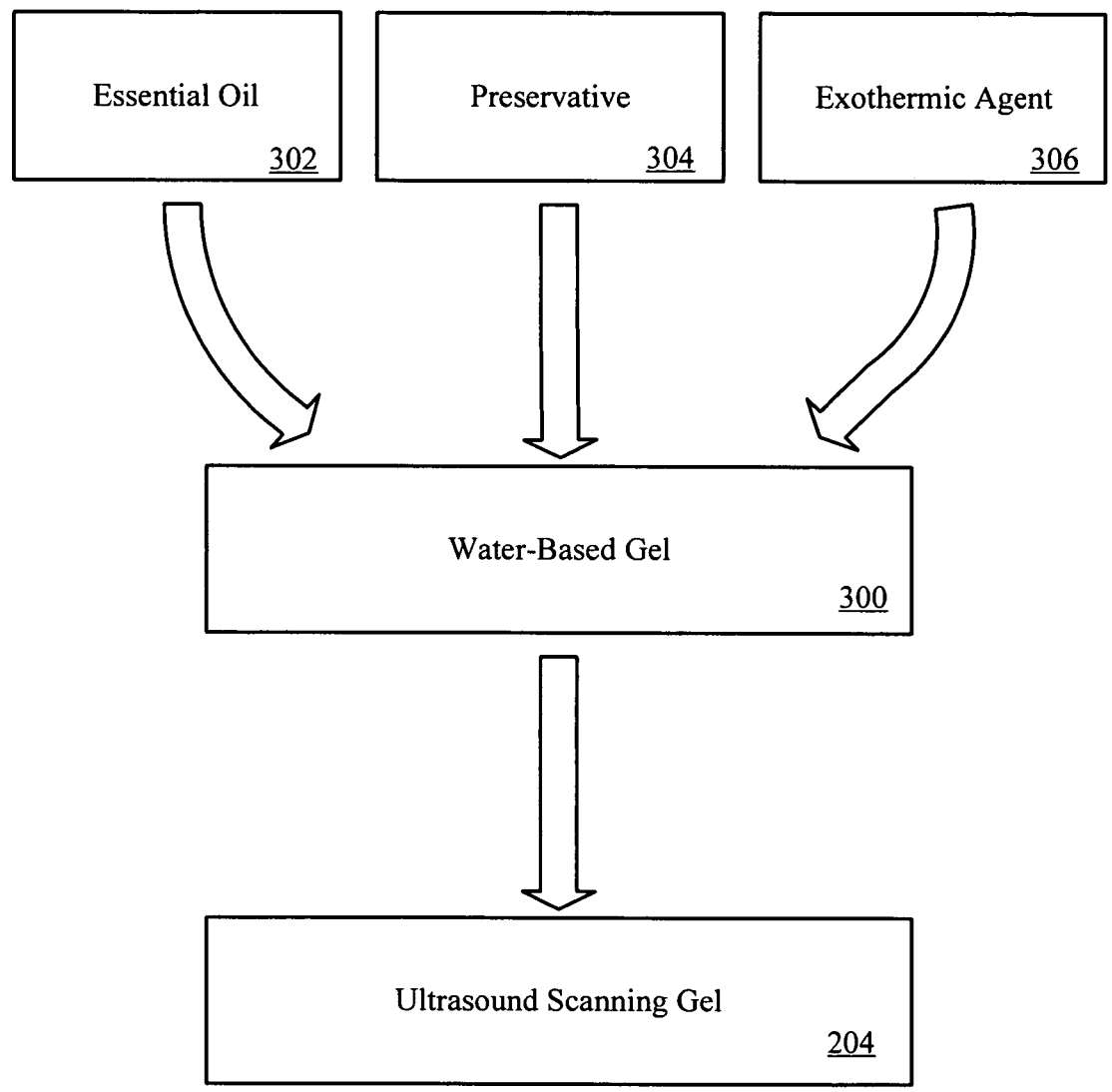
FIG. 3 is a schematic block diagram of one embodiment of an ultrasound transmission gel in accordance with the present invention.

Referring now to FIG. 3, an ultrasound transmission gel 204 in accordance with the present invention may comprise, for example, a water-based gel 300 and at least one essential oil 302. In certain embodiments, an ultrasound transmission gel 204 may further include an exothermic agent 306 and/or a preservative 304 to impart a longer transmission gel 240 shelf-life, where the exothermic agent 306 may generate and retain warmth upon application of the ultrasound transmission gel 204 to a patient's skin 200. An exothermic agent may comprise, for example, methyl salicylate, phosphate derivatives, vanillyl derivatives, ethanol, niacin, eucalyptus oil, cinnamon cassia (cinnamon), zingiber officinalis (ginger), mint, sandalwood, orange, clove, amara (almond), persica gratissima (avocado oil), cannabis sativa (hemp) seed oil, aloe vera, or any other exothermic agent known to those in the art. Alternatively, an exothermic agent may comprise a heat-generating medium consisting of carbon, iron, water and/or salt which is activated upon contact with oxygen in the air.

A water-based gel 300 may comprise, for example, a substantially hypoallergenic, bacteriostatic, non-sensitizing, non-irritating formula such as the water-based gel manufactured by Parker Laboratories, New Jersey, known as Aqua-Sonic® 100, or other such water-based gel known to those in the art. AquaSonic® 100 consists of water, Germall® Plus (Diazolidinyl Urea ("DU") and Iodopropynyl Butylcarbamate ("IPBC")), methyl paraben, carbomer, and Triethanolamine ("TEA") 85%.

An essential oil 302 may be added to the water-based gel 300 to provide a certain beneficial effect to a patient, such as to bring about a sense of relaxation and peace, relieve stress and pain, and in some cases, heal illnesses. Indeed, aromatherapy and essential oils 302 have been used for many years as natural healing agents. While properties of essential oils 302 vary, as discussed in more detail with reference to FIG. 4 below, essential oils 302 generally function to stimulate the limbic system through the olfactory nerves, and/or may be absorbed through the skin to circulate the effects of the oils 302 throughout the body. Essential oils 302 typically have a positive effect on an individual's well being and may be used to treat humans as well as animals.

Inclusion of one or more essential oils 302 in an ultrasound transmission gel 204 in accordance with the present invention may reduce a patient's apprehension and/or discomfort during an ultrasound imaging procedure or an ultrasound transmission procedure. Further, by inducing relaxation and pain relief, the present invention facilitates an operator's ability to obtain quick and accurate ultrasound signal data from a steady, relaxed subject. Of course, one skilled in the art will recognize that precautions should be taken to ensure that no essential oil 302 added to a water-based gel 300 in accordance with the present invention will have an adverse effect on a patient or fetus, as the case may be.

An exothermic agent 306 such as cinnamon cassia (cinnamon), zingiber officinalis (ginger), mint, sandalwood, orange, clove, amara (almond), persica gratissima (avocado oil), cannabis sativa (hemp) seed oil, aloe vera, or any other exothermic agent known to those in the art, may be included in an ultrasound transmission gel 204 in accordance with the present invention to alleviate a perception of cold upon application of the ultrasound transmission gel 204 and throughout an ultrasound imaging procedure or an ultrasound transmission procedure, thus facilitating patient comfort and relaxation. In particular, in certain embodiments an exothermic agent 306 may be activated to generate heat upon exposure to oxygen in the air, or by any other mechanism known to those in the art. In some embodiments, a quantity of an exothermic agent 306 may be precisely controlled and may be formulated to retain heat over time for a patient's maximum enjoyment and relaxation. In this manner, an ultrasound transmission gel 204 that includes an exothermic agent 306 in accordance with the present invention improves and simplifies use of a transmission gel during an ultrasound procedure. Specifically, because an exothermic agent 306 is included in the ultrasound transmission gel 204 itself and is self-actuating, no external warming apparatus or additional steps to warm the ultrasound transmission gel 204 are needed. Moreover, the increased comfort experienced by a patient as a result of warmth generated by the exothermic agent 306 promotes quick and accurate ultrasound imaging results by reducing a risk of unanticipated movement by a patient that is tense or in pain.

Referring now to FIG. 4, essential oils 302 that may be used in accordance with certain embodiments of the present invention may include oils 302 having properties 402 that induce tranquility, relaxation, restfulness or peacefulness, such as chamomile, sandalwood, lavender, rosewood, tangerine or any other essential oil 302 known to those in the art. In other embodiments, oils 302 may be selected for properties 402 specific to certain medical conditions, such as geranium, clary sage, grapefruit and orange to act as antidepressants, orange to act as an antispasmodic, geranium to act as a diuretic and for hormone balance, balsam for skin care, peppermint to aid respiration, and other essential oils 302 having properties 402 known to those in the art.

In certain embodiments, an ultrasound transmission gel 204 in accordance with the present invention may be customized to a particular patient depending on essential oils 302 selected for addition thereto. For example, a patient suffering from premenstrual syndrome or other hormonal problem may benefit from an ultrasound transmission gel 204 including a combination of geranium, clary sage and orange to relieve symptoms such as reduced vitality, water retention, and cramps.

Figure 5:
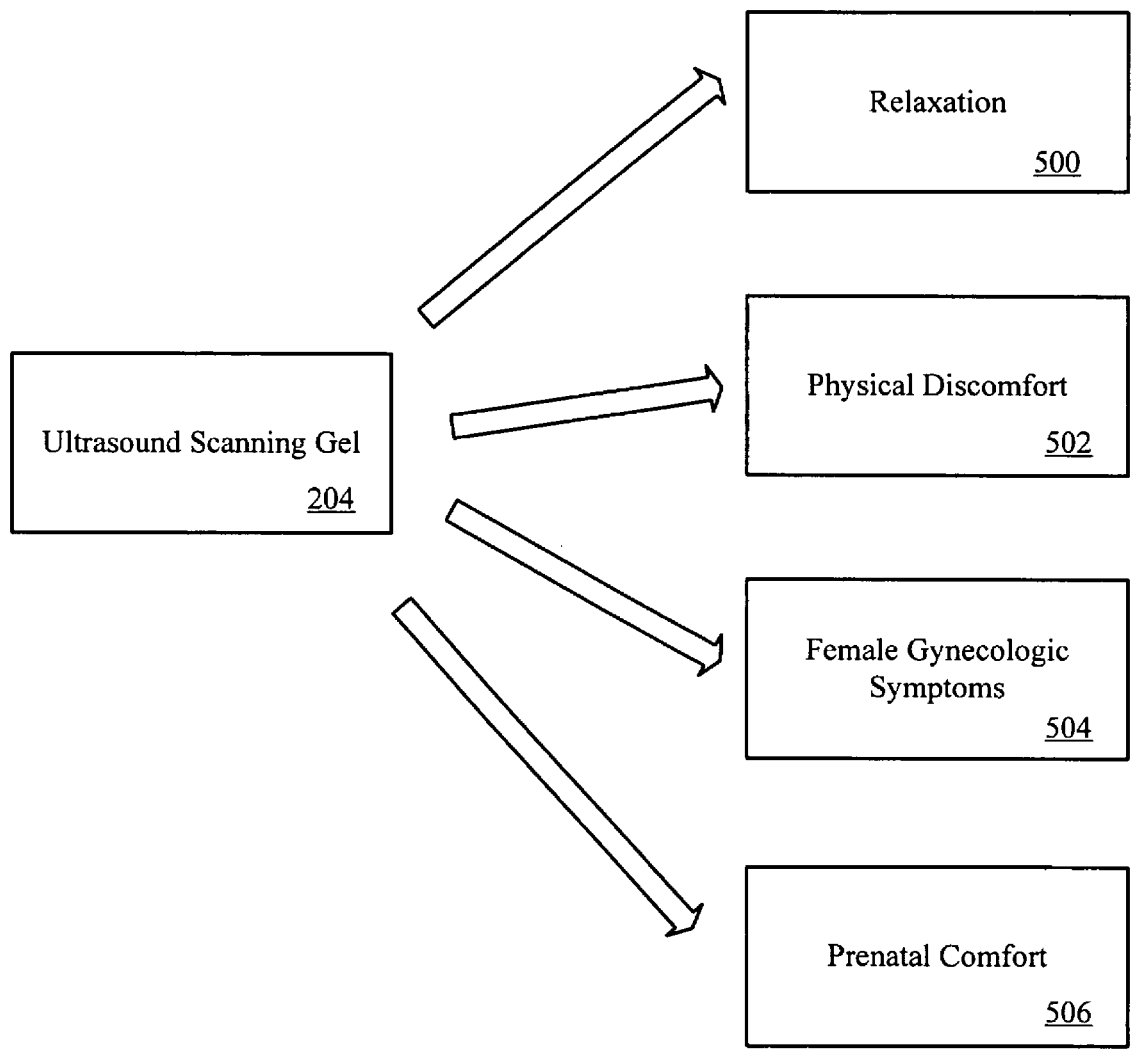
FIG. 5 is a schematic block diagram of applications of an ultrasound transmission gel in accordance with certain embodiments of the present invention.

Referring now to FIG. 5, an ultrasound transmission gel 204 may be broadly categorized according to its general effects on a patient. A first category 500 may include, for example, ultrasound transmission gels 204 that induce relaxation in a patient. As mentioned above, such ultrasound transmission gels 204 may include chamomile, lavender, parsley, or any other essential oil 302 known to those in the art capable of inducing relaxation in a patient. A second category 502 may include ultrasound transmission gels 204 adapted to relieve physical discomfort. Such ultrasound transmission gels 204 may include, for example, essential oils 302 such as birch sweet to act as an anti-inflammatory, cinnamon to aid digestion, myrtle to act as an expectorant, peppermint or violet leaf to aid respiration, or any other essential oil 302 known to those in the art having properties 402 to relieve physical discomfort. A third category 504 may include ultrasound transmission gels 204 capable of treating female hormonal and/or gynecologic symptoms. Such ultrasound transmission gels 204 may include, for example, essential oils 302 such as geranium, clary sage, orange, parsley, rose geranium, or any other essential oil 302 known to those in the art having properties 402 to relieve female hormonal and/or gynecologic symptoms. A fourth category 506 may include ultrasound transmission gels 204 that comfort mother and baby during a prenatal ultrasound imaging procedure. Such ultrasound transmission gels 204 may include, for example, essential oils 302 such as vanilla to impart a feeling of security, sage for rejuvenation, cinnamon to aid digestion, and other essential oils 302 known to those in the art having properties 402 that provide comfort and security to mother and baby. Of course, one skilled in the art will recognize that ultrasound transmission gels 204 in any category may further include an exothermic agent 306 and/or preservative as discussed in detail above.

Figure 6:
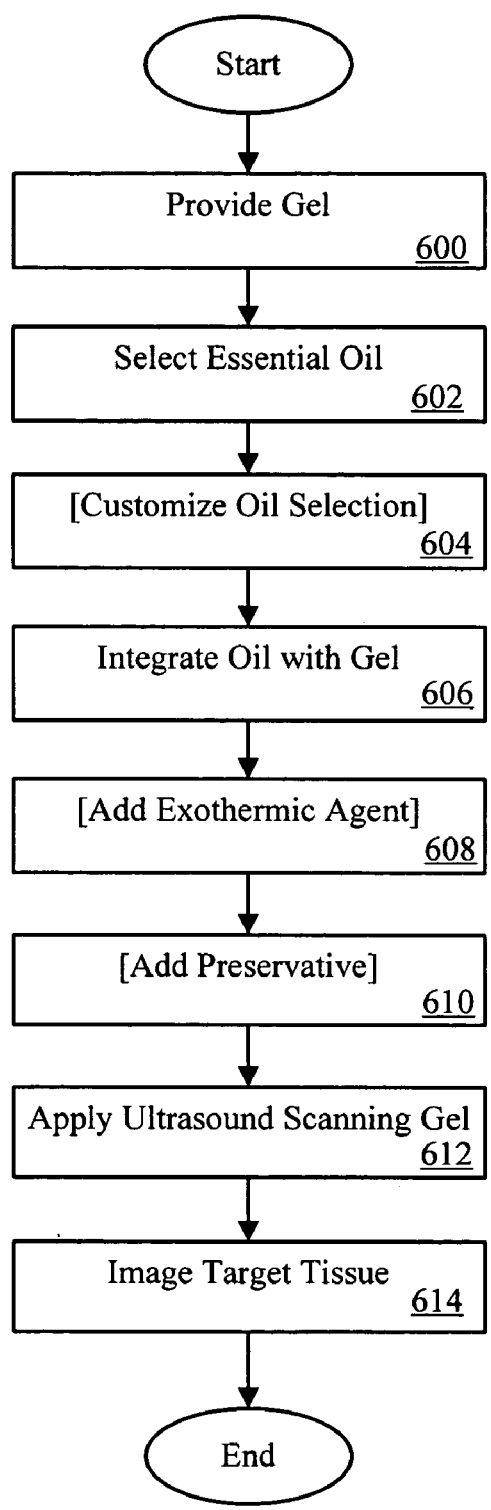
FIG. 6 is a flow chart detailing steps for performing an ultrasound imaging procedure in accordance with certain embodiments of the present invention.

Referring now to FIG. 6, a method for performing an ultrasound imaging procedure in accordance with certain embodiments of the present invention may include providing 600 a water-soluble gel and selecting 602 one or more essential oils for addition to the water-soluble gel. As discussed above, an essential oil selected for implementation in accordance with the present invention may have properties capable of calming, relaxing or relieving pain to both facilitate a patient's comfort and facilitate accurate ultrasound imaging results. In some embodiments, a method in accordance with the present invention may include customizing 604 a selection of essential oils depending on a particular patient's medical condition.

A method may further include integrating 606 the selected essential oils with the water-based gel, and optionally adding 608 an exothermic agent to the composition to further increase a patient's comfort during an ultrasound imaging procedure. In some embodiments, a preservative may also be added 610 to facilitate a longer shelf-life of the ultrasound transmission gel of the present invention by imparting an additional guarantee against microbial growth. A preservative may be selected from preservatives known to those of skill in the art, including one or more of methylparaben, benzoic acid, sorbic acid, gallic acid, propylparaben, or the like. The ultrasound transmission gel may then be applied 612 to an area of a patient's skin substantially corresponding to a target tissue area subjacent the epidermal layer. The ultrasound transmission gel may function to eliminate interference between a patient and ultrasound scanning equipment such that ultrasound scanning equipment can then be used to accurately image 614 the target tissue.

We claim:

1. An ultrasound transmission gel for topical application to a patient, consisting of:
    a water-soluble gel having a conductivity adapted to facilitate ultrasound signal transfer between a probe and a target tissue area in a patient, wherein the water-soluble gel consists of water, Diazolidinyl Urea ("DU"), Iodopropynyl Butylcarbamate ("IPBC"), methyl paraben, carbomer, and Triethanolamine ("TEA") 85%; and
    an essential oil in a range from about one percent to about five percent of a total composition weight of the ultrasound transmission gel, wherein the essential oil has properties that induce at least one of a palliative effect and a therapeutic effect in the patient;
    wherein the ultrasound transmission gel has a composition that preserves pigmentation of an area of skin of the patient on which the ultrasound transmission gel is applied.

2. The ultrasound transmission gel of claim 1, wherein the essential oil is selected from the group consisting of balsam, chamomile, lavender, orange, geranium, grapefruit, rosewood, sage, sandalwood, tangerine, vanilla, ylang ylang, palma rosa, elemi, geranium, patchouli, rose, clary sage, and bergamot.

3. The ultrasound transmission gel of claim 1, wherein the water-soluble gel is at least one of substantially colorless, substantially hypoallergenic, and non-staining.

4. The ultrasound transmission gel of claim 1, wherein the palliative effect is selected from the group consisting of relaxation, stress relief, anxiety alleviation and mother and baby comfort.

5. The ultrasound transmission gel of claim 1, wherein the therapeutic effect is selected from the group consisting of pain relief, stretch mark reduction, nausea alleviation, increased vitality, and encouraged healing.

6. The ultrasound transmission gel of claim 1, wherein the ultrasound transmission gel is customized with the essential oil to alleviate a particular medical condition of the patient.

* * * * *